(12) United States Patent
Clendinning et al.

(10) Patent No.: US 10,466,101 B2
(45) Date of Patent: Nov. 5, 2019

(54) REFERENCE LIGHT ADJUSTMENT METHOD FOR SPECTROMETER BASED MEASUREMENT OR CONTROL SYSTEMS

(71) Applicant: Ocean Optics, Inc., Largo, FL (US)

(72) Inventors: Kirk Clendinning, Winter Springs, FL (US); Nelson Chandler, Winter Park, FL (US)

(73) Assignee: OCEAN OPTICS, INC., Largo, FL (US)

( * ) Notice: Subject to any disclaimer, the term of this patent is extended or adjusted under 35 U.S.C. 154(b) by 0 days.

(21) Appl. No.: 16/017,069

(22) Filed: Jun. 25, 2018

(65) Prior Publication Data

US 2019/0003886 A1  Jan. 3, 2019

Related U.S. Application Data

(60) Provisional application No. 62/525,799, filed on Jun. 28, 2017.

(51) Int. Cl.
*G01J 3/02* (2006.01)
*G01J 3/10* (2006.01)
*G01J 3/28* (2006.01)
*G01N 21/25* (2006.01)

(52) U.S. Cl.
CPC .............. *G01J 3/0237* (2013.01); *G01J 3/10* (2013.01); *G01J 3/28* (2013.01); *G01N 21/255* (2013.01)

(58) Field of Classification Search
CPC ........ G01J 3/02; G01J 3/10; G01J 3/28; G01J 3/0237; G01N 21/255; G01V 8/24; G06T 7/00

See application file for complete search history.

(56) References Cited

U.S. PATENT DOCUMENTS

2011/0108719 A1* 5/2011 Ford ..................... G01J 3/02
250/262
2015/0369664 A1* 12/2015 Garsha .................. G01J 3/10
356/402

* cited by examiner

*Primary Examiner* — Jamil Ahmed
(74) *Attorney, Agent, or Firm* — Perkins Coie LLP

(57) ABSTRACT

A method to adjust the energy transmitted from a multiplicity of light sources to provide an adequate reference for spectral measurement or control using a multichannel feedback adjustment algorithm that compensates for the interactions between adjacent spectral ranges and sets reference light sources for optimal system performance using a normalized energy value for each spectral range is disclosed.

12 Claims, 2 Drawing Sheets

REFERENCE LIGHT ADJUSTMENT METHOD FOR SPECTROMETER BASED MEASUREMENT OR CONTROL SYSTEMS

CROSS-REFERENCE TO RELATED APPLICATION

The present application claims the benefit of previously filed Provisional Patent Application, Ser. No. 62/525,799, filed on Jun. 28, 2017.

FIELD OF THE INVENTION

The method of this disclosure belongs to the field of sample measurements or control systems using spectrometers. More specifically it is a method using a multichannel feedback adjustment system to modify the energy transmitted from a multiplicity of light sources, such that an adequate reference value (in counts, which represent quantities of light energy) is provided for each pixel (or range of wavelengths) of a spectrometer being used as a component in a measurement or control system.

BACKGROUND OF THE INVENTION

The optical path for a typical spectrometer based measurement or control system exhibits change due to mechanical variances caused by temperature, vibration, shock or wear. Examples of these changes include: optical variations, such as fiber solarization or lens deposits among others; and electrical drift from temperature changes, component aging or design tolerances. Providing consistent reference values for all pixels across the spectrum of interest improves system stability, increases mean time between maintenance, raises robustness, and can reduce component cost. The most common method for establishing light source intensity is to set the integration time of the spectrometer such that the most intense wavelength results in a count value slightly less than the saturation count for that pixel. Of course the remaining pixels then suffer from lower signal to noise ratios. Thus, a method that ensures consistent and appropriate reference light source intensity for a spectrometer based measurement or control system is needed.

BRIEF SUMMARY OF THE INVENTION

This application discloses a multichannel feedback adjustment system that modifies the energy transmitted from a multiplicity of light sources to provide an adequate reference intensity for spectral measurement or control systems. A control algorithm compensates for the interactions between adjacent spectral ranges and sets the intensity of the reference light sources for optimal system performance.

BRIEF DESCRIPTION OF THE DRAWINGS

For a fuller understanding of the nature and objects of the invention, reference should be made to the following detailed description, taken in connection with the accompanying drawings, in which.

DESCRIPTION OF THE PREFERRED EMBODIMENT

The method of this disclosure provides a mechanism by which the reference light energy for a spectrometer based measurement or control system is adjusted appropriately for spectral ranges of interest, such that the counts reported by the spectrometer are consistent (and near saturation counts) during its usage duty cycle.

Figure 1:
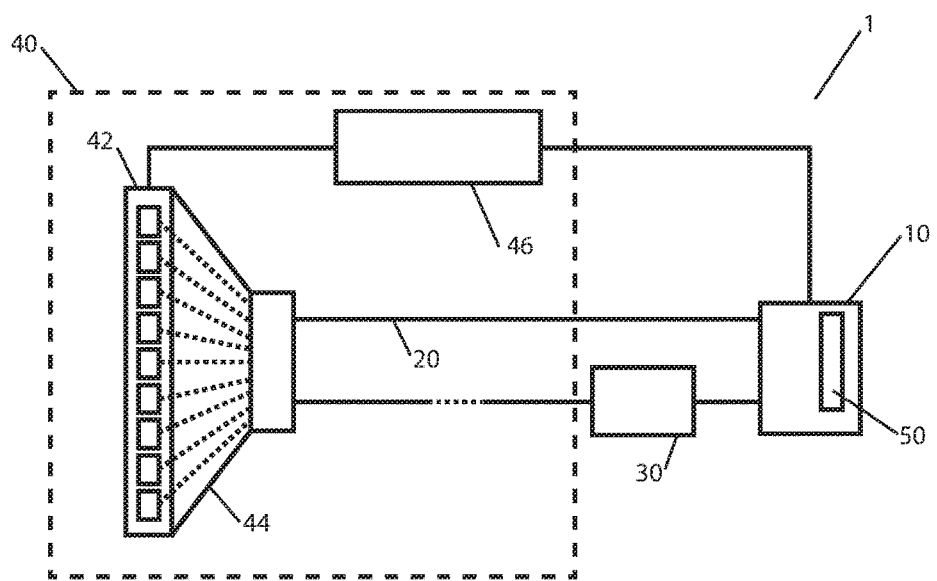
FIG. 1 shows a prior art spectrometer system with a multispectral light source; and, FIG. 2 is a diagram of the feedback method of the preferred embodiment.
Figure 2:
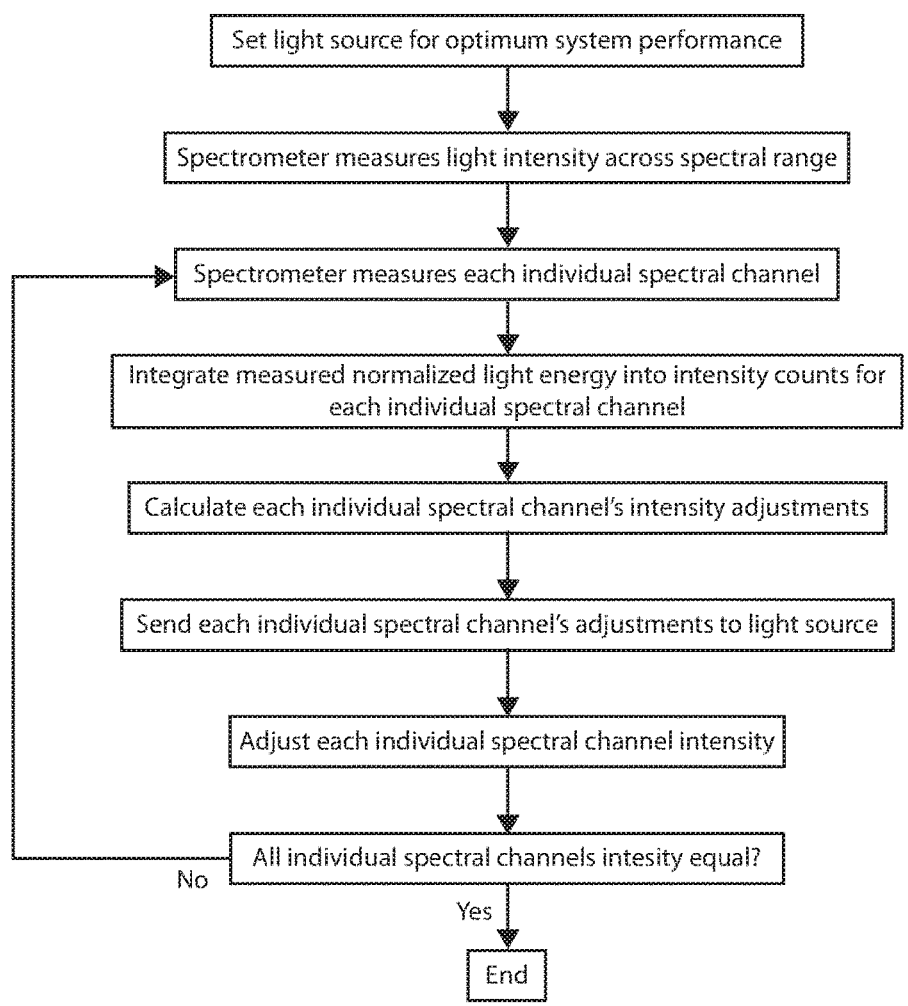

The preferred embodiment of the disclosed method achieves the aforementioned purpose by implementing a control circuit (46) feedback loop in a spectral measurement or control system (1) formed by a spectrometer (10), a light delivery optical system (20), the system under test (30) and an individual spectral channel adjustable multispectral light source (40) as shown in FIG. 1 The method, as shown in FIG. 2, is as follows: At the beginning of each control or measurement period, the reference source light (42) intensity is set for optimal spectral measurement or control system (1) performance. During this reference step, the spectrometer (10) measures light intensity across its entire spectral range. It then integrates the normalized energy measured for each adjacent spectral channel (44) represented by the adjustable multispectral light source (40). Adjacent spectral channel (44) adjustments are calculated and intensity settings sent via the control circuitry (46) to the reference light source (42). Then once again, the light is measured, adjacent spectral channel (44) adjustment calculations are made and settings sent. When the values settle, the intensity counts for each individual spectral channel (44) should be similar. Thus, rather than adjusting the spectrometer (10) integration time to compensate for losses in the optical spectral measurement or control system (1), the reference light source (42) individual spectral channel (44) intensities are adjusted.

Through the use of this multichannel feedback method a spectrometer (10) based spectral measurement or control system (1) can be kept at a high level of performance automatically, eliminating the need for users to understand the complexities of the optical system.

More specifically in the preferred embodiment the number of counts for each pixel at the detector (50) in the spectrometer (10) can be thought of as representing a normalized energy. Given a target value for a spectral channel (44) of interest, the corresponding reference light source (42) intensity is then set to cancel losses in the spectral measurement or control system's (1) optical path (20). Rather than independently ramping the value of each spectral channel (44) to match losses, as is typical in the prior art, a multichannel feedback adjustment algorithm compensates for the effects of light energy from adjacent spectral channels (44). All individual spectral channels (44) are adjusted simultaneously to account for interactions between them resulting in more repeatable settings. By using a feedback system control circuit (46), such as a multichannel Proportional-Integral-Derivative controller, well known by those skilled in the art, the effects of adjacent spectral channels (44) are essentially eliminated when the loop reaches equilibrium reducing the need for complex iterative calculations.

Identified user issues which will be solved by the disclosed feedback method include: Spectrometer, fiber, and light source response is different from unit to unit; fibers degrade over time, at different wavelengths and at different rates; light sources degrade over time at different wavelengths and at different rates; and users need to understand all of this and make allowances for these variations at the system level.

By using the intensity counts from the spectrometer (10) detector (50) to adjust the input levels of the reference light source intensity at each spectral channel (44), the spectrometer measurement or control system (1) will automatically be able to adjust for differences in the response of each spectrometer (10) quickly and easily without technical knowledge. It will also adjust as fibers or light sources degrade, by increasing the energy in the specific wavelengths that have suffered decreased intensity. This frees a user from thinking about how the light source (40), fiber (20), and spectrometer (10) efficiencies interplay and how they change over time, allowing for quick customization of a spectrum profile, while taking into account all three subsystems of a typical spectrometer measurement or control system (1). For example, this method comprehends different spectrum profiles for different measurements in the same system (i.e. only turn on the 350 nm LED if the measurement requires an absorption spectrum in that spectral range, and later the 500-600 nm LED for separate absorption spectrum so that there is no interaction).

Since certain changes may be made in the above described method for using a multichannel feedback adjustment algorithm for adjusting a reference light source without departing from the scope of the invention herein involved, it is intended that all matter contained in the description thereof shall be interpreted as illustrative and not in a limiting sense.

What is claimed is:

1. A method for adjusting an adjustable multiple spectral channel reference light source prior to starting a control or measurement period by implementing a feedback loop formed by a spectrometer, a light delivery optical system, a system under test, and an adjustable multiple spectral channel reference light source comprising:

first, without placing the system under test between said spectrometer and said adjustable multiple spectral channel reference light source, at the beginning of each control or measurement period, operating said adjustable multiple spectral channel reference light source to set output light intensity levels at different individual spectral channels across said spectrometer's entire spectral range;

then operating said spectrometer to measure light intensity levels at different individual spectral channels across said spectrometer's entire spectral range by measuring each individual spectral channel of said adjustable multiple spectral channel reference light source's quantities of normalized light energy at said different individual spectral channels, respectively, and integrating said normalized light energy measured into intensity counts for each individual spectral channel contained in said adjustable multiple spectral channel reference light source;

then calculating each said individual spectral channel's intensity adjustments;

then sending said each said individual spectral channel's intensity adjustments to said adjustable multiple spectral channel reference light source;

then simultaneously adjusting each of said individual spectral channel's intensity of said adjustable multiple spectral channel reference light source;

then repeating said individual spectral channel measuring, said spectral intensity adjustment calculating, said sending of calculated adjustments, and said adjusting steps one or more times until said intensity counts for respectively for said different individual spectral channels contained in said adjustable multiple spectral channel reference light source are similar;

subsequently in a measurement period, placing the system under test between said spectrometer and said adjustable multiple spectral channel reference light source to be illuminated by light from said adjustable multiple spectral channel reference light source under said similar intensity counts respectively for said individual spectral channels contained in said adjustable multiple spectral channel reference light source; and operating said spectrometer in said measurement period to measure received light intensity levels of light after passing through the system under the test at said different individual spectral channels, respectively.

2. The method as in claim 1, wherein, prior to said measurement period, simultaneously adjusting each of said individual spectral channel's intensity of said adjustable multiple spectral channel reference light source to set said intensity counts for respectively for said different individual spectral channels to be below but near a detection saturation count at each individual spectral channel.

3. The method as in claim 1, wherein, prior to said measurement period, simultaneously adjusting each of said individual spectral channel's intensity of said adjustable multiple spectral channel reference light source without adjusting an integration time in detection of any particular individual spectral channel by said spectrometer.

4. The method as in claim 1, wherein, prior to said measurement period, simultaneously adjusting each of said individual spectral channel's intensity of said adjustable multiple spectral channel reference light source without adjusting an integration time in detection by said spectrometer.

5. The method as in claim 1, wherein, prior to said measurement period, repeating said individual spectral channel measuring, said spectral intensity adjustment calculating, said sending of calculated adjustments, and said adjusting steps one or more times until said intensity counts for respectively for said different individual spectral channels contained in said adjustable multiple spectral channel reference light source are similar so as to reduce an impact to measurement accuracy due to variances caused by temperature, vibration, shock or wear.

6. The method as in claim 1, wherein, prior to said measurement period, repeating said individual spectral channel measuring, said spectral intensity adjustment calculating, said sending of calculated adjustments, and said adjusting steps one or more times until said intensity counts for respectively for said different individual spectral channels contained in said adjustable multiple spectral channel reference light source are similar so as to reduce an impact to measurement accuracy due to channel variations between said different individual spectral channels.

7. The method as in claim 1, wherein, prior to said measurement period, repeating said individual spectral channel measuring, said spectral intensity adjustment calculating, said sending of calculated adjustments, and said adjusting steps one or more times until said intensity counts for respectively for said different individual spectral channels contained in said adjustable multiple spectral channel reference light source are similar so as to reduce an impact to measurement accuracy due to channel variations between said different individual spectral channels in optical paths for guiding light from said adjustable multiple spectral channel reference light source to optical detectors in said spectrometer.

8. The method as in claim 1, wherein, prior to said measurement period, repeating said individual spectral channel measuring, said spectral intensity adjustment calculating, said sending of calculated adjustments, and said adjusting steps one or more times until said intensity counts for respectively for said different individual spectral channels contained in said adjustable multiple spectral channel reference light source are similar so as to reduce an impact to measurement accuracy due to aging of one or more components over time.

9. The method as in claim 1, wherein, prior to said measurement period, repeating said individual spectral channel measuring, said spectral intensity adjustment calculating, said sending of calculated adjustments, and said adjusting steps one or more times until said intensity counts for respectively for said different individual spectral channels contained in said adjustable multiple spectral channel reference light source are similar so as to reduce an impact to measurement accuracy due to differences in interaction of one or more components with light at different optical wavelengths of said different individual channels.

10. A method for optically measuring a system under test, comprising:
    providing an adjustable multiple spectral channel reference light source to produce probe light at different individual spectral channels, a light delivery optical system optically coupled to receive the probe light and to direct the probe light to illuminate the system under test, and a spectrometer containing different optical detectors for detecting optical signals of the different individual spectral channels, respectively;
    preforming a pre-measurement adjustment operation of the adjustable multiple spectral channel reference light source to adjust output light levels of the probe light at the different individual spectral channels without placing the system under test between the spectrometer and the adjustable multiple spectral channel reference light source to achieve optimized output light levels of the probe light at the different individual spectral channels for optically measuring the system under test after completion of the pre-measurement adjustment operation;
    subsequent to the pre-measurement adjustment operation, placing the system under test in an optical path of the probe light between the adjustable multiple spectral channel reference light source and the spectrometer; and
    operating the adjustable multiple spectral channel reference light source to produce the probe light at the optimized output light levels of at the different individual spectral channels to illuminate the system under test and to obtain optical measurements of the system under test at the different individual spectral channels,
    wherein the pre-measurement adjustment operation includes:
        operating the adjustable multiple spectral channel reference light source to produce the probe light at initial output light levels at the different individual spectral channels, without placing the system under test to be illuminated by the probe light,
        measuring detector output signals from the different optical detectors in the spectrometer respectively for the different individual spectral channels,
        based on the measured levels of the detector output signals respectively for the different individual spectral channels, adjusting the output light levels of the probe light at the different individual spectral channels produced by the adjustable multiple spectral channel reference light source to cause the measured signal levels of the detector output signals from the different optical detectors in the spectrometer respectively for the different individual spectral channels to be similar to one another, and
        setting the adjusted output light levels of the probe light at the different individual spectral channels that cause the measured signal levels of the detector output signals from the different optical detectors in the spectrometer respectively for the different individual spectral channels to be similar to one another as the optimized output light levels of the probe light at the different individual spectral channels.

11. The method as in claim 10, wherein, in the pre-measurement adjustment operation, adjusting adjust the output light levels of the probe light at the different individual spectral channels so that the detector signal levels from the optical detectors of the spectrometer are below but near a detection saturation level.

12. The method as in claim 10, wherein, in the pre-measurement adjustment operation, adjusting the output light levels of the probe light at the different individual spectral channels to reduce an impact to measurement accuracy due to variances caused by temperature, vibration, shock or wear, channel variations between said different individual spectral channels, or differences in interaction of one or more components with the probe light at different optical wavelengths of the different individual channels.

* * * * *